(12) United States Patent
Bergfjord

(10) Patent No.: US 10,653,895 B2
(45) Date of Patent: May 19, 2020

(54) RADIOTHERAPY APPARATUS

(71) Applicant: Elekta AB (publ), Stockholm (SE)

(72) Inventor: Per Harald Bergfjord, West Sussex (GB)

(73) Assignee: ELEKTA AB (PUBL), Stockholm (SE)

( * ) Notice: Subject to any disclaimer, the term of this patent is extended or adjusted under 35 U.S.C. 154(b) by 331 days.

(21) Appl. No.: 15/550,007

(22) PCT Filed: Feb. 2, 2016

(86) PCT No.: PCT/EP2016/052178
§ 371 (c)(1),
(2) Date: Aug. 9, 2017

(87) PCT Pub. No.: WO2016/128255
PCT Pub. Date: Aug. 18, 2016

(65) Prior Publication Data
US 2018/0021598 A1 Jan. 25, 2018

(30) Foreign Application Priority Data
Feb. 10, 2015 (GB) .................................. 1502145.4

(51) Int. Cl.
*A61N 5/10* (2006.01)
*A61B 6/00* (2006.01)

(52) U.S. Cl.
CPC .......... *A61N 5/1082* (2013.01); *A61B 6/4435* (2013.01); *A61N 5/1049* (2013.01); *A61N 2005/1061* (2013.01)

(58) Field of Classification Search
CPC ............... A61N 5/1082; A61N 5/1049; A61N 2005/1061; A61B 6/4435

USPC .......................................................... 378/65
See application file for complete search history.

(56) References Cited

U.S. PATENT DOCUMENTS

| | | | |
|---|---|---|---|
| 2004/0005027 A1* | 1/2004 | Nafstadius | ........... A61N 5/1049 378/65 |
| 2013/0158382 A1 | 6/2013 | Chao | |
| 2014/0171725 A1 | 6/2014 | Adler et al. | |

OTHER PUBLICATIONS

International Search Report for International Application No. PCT/EP2016/052178 from the European Patent Office, dated Apr. 1, 2016.

(Continued)

*Primary Examiner* — Courtney D Thomas
(74) *Attorney, Agent, or Firm* — Finnegan, Henderson, Farabow, Garrett & Dunner, L.L.P.

(57) ABSTRACT

A radiotherapy apparatus includes a fixed support and a gantry including a chassis part and a source part, the chassis part being rotatably attached to the fixed support to allow rotation thereof about a generally horizontal axis, and the source part being connected to the chassis part via a rotatable connection allowing the source part to rotate relative to the chassis part around a transverse axis. The source part includes a source of therapeutic radiation directed towards the intersection of the transverse axis and the horizontal axis. The chassis part and the source part together define an annular ring that encircles the horizontal axis. In this way, the radiotherapy apparatus can provide the full usual range of treatments, but can also adapt itself to adopt a non-coplanar geometry when required, for example to treat difficult locations in the head and neck.

17 Claims, 1 Drawing Sheet

(56) References Cited

OTHER PUBLICATIONS

Written Opinion of the International Searching Authority for International Application No. PCT/EP2016/052178 from the European Patent Office.

* cited by examiner

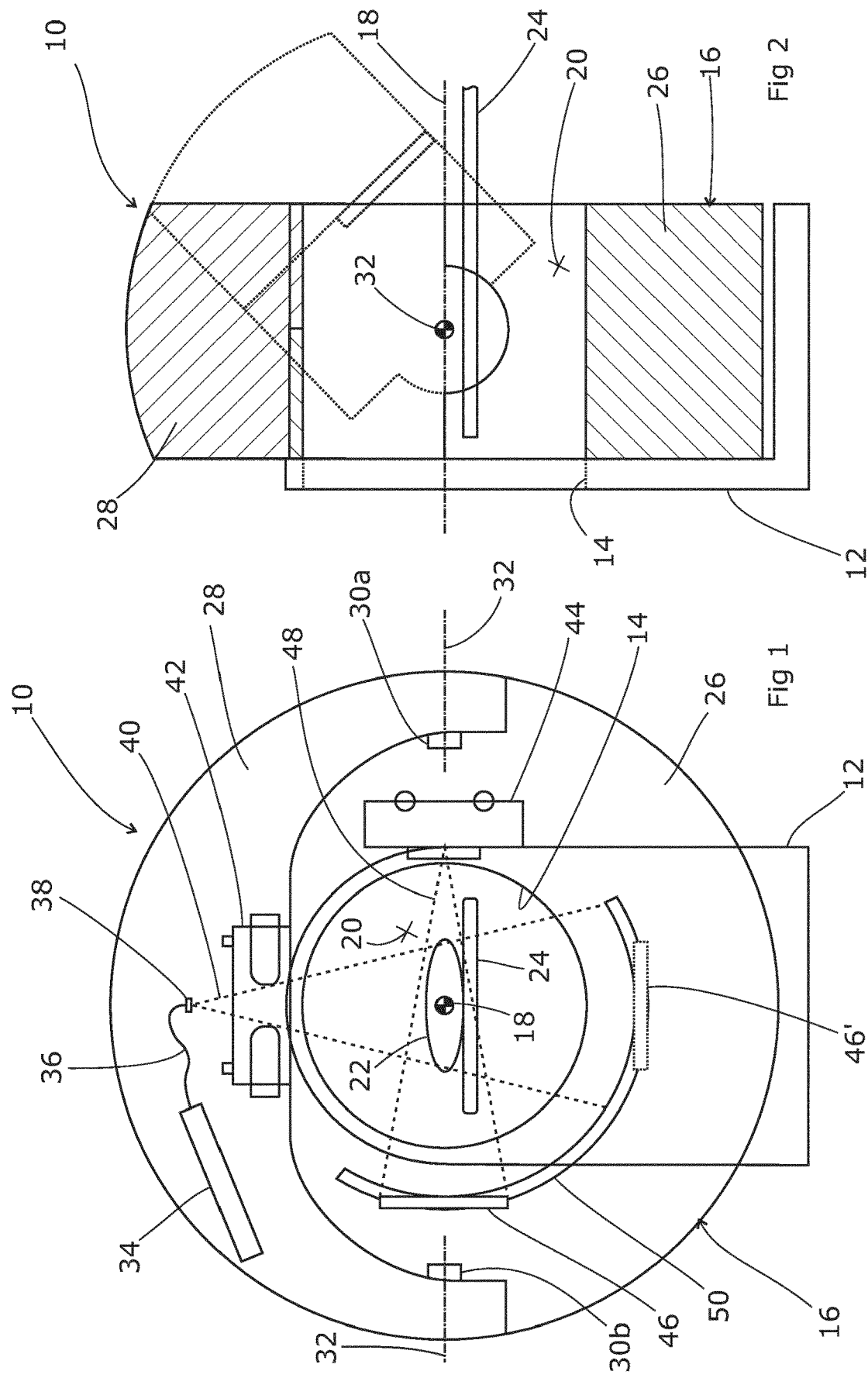

RADIOTHERAPY APPARATUS

CROSS-REFERENCE TO RELATED PATENT APPLICATIONS

This application is a U.S. national stage entry under 35 U.S.C. § 371 of International Application No, PCT/EP2016/052178, filed Feb. 2, 2016, which claim the benefit of United Kingdom Patent Application No. 1502145.4, filed Feb. 10, 2015, all of which are hereby incorporated by reference in their entirety.

FIELD OF THE INVENTION

The present invention relates to radiotherapy apparatus.

BACKGROUND ART

Radiotherapeutic apparatus is well-known, and consists of a source of radiation which emits a beam of radiation that is directed toward a patient in order to destroy or otherwise harm tumourous cells within the patient. Usually, the beam is collimated in order to limit its spatial extent to a desired region within the patient, usually the tumour or a sub-section of the tumour. The source can be a linear accelerator for high-energy (MV) x-radiation, or an isotopic source such as Co-60.

The source is often rotated around the patient in order to irradiate the desired region from a number of different directions, thereby reducing the dose applied to healthy tissue around the desired region. The shape of the defined desired region can change dynamically as the source rotates, in order to build up a complex dose distribution for tumours with more challenging shapes and/or which are located near to sensitive areas.

As the dose distribution becomes more closely tied to the exact shape of the tumour, and as the accuracy of the dose delivery improves, it has become necessary to know the current position of the patient, their internal organs, and the tumour with greater accuracy. As a result, low-energy x-ray sources are often provided on the apparatus in addition to the high-energy therapeutic source, to allow for x-ray or CT imaging of the patient before or during treatment. Portal imagers are often provided, which detect the therapeutic beam after attenuation by the patient.

Various configurations exist for the radiation source. One common arrangement is for the source to be mounted on the end of an arm that extends away from a large upright cylindrical gantry that is rotatable around its horizontal axis. The arm is located off-centre with respect to the gantry, and the source directs the beam of radiation towards the axis. In this way, as the gantry rotates, the source irradiates the point at which the beam and the rotation axis meet (the "isocentre") from all directions.

Another is shown in US2013/0158382A1, in which a source is located within a rotateable section of an annular ring disposed around the patient. The fixed part of the ring is mounted at its base onto a support so as to allow it to be tilted away from a vertical orientation; thus, as the source rotates it irradiates the isocentre from all angles, whereas tilting the ring allows the plane in which the various irradiation directions lie to be varied. However, tilting the ring moves the centre of the ring, thus moving the isocentre and meaning that either all treatment during a particular treatment fraction needs to be at a single tilt angle, or the position of the patient needs to be adjusted during a treatment fraction.

Our previous publication WO2005/041774A1 discloses a radiotherapy apparatus in which the source is mounted on a rotateable ring, via a rotateable union that allows the source to rotate around an axis that is perpendicular to the rotation axis of the ring, which emits a beam collimated towards the intersection of the two rotation axes. Thus, as the ring rotates, the source irradiates a single point along a direction lying on the surface of a cone whose enclosed angle is determined by the angle between the source and the ring.

SUMMARY OF THE INVENTION

The present invention therefore provides a radiotherapy apparatus comprising a fixed support, and a gantry comprising a chassis part and a source part, the chassis part being rotatably attached to the fixed support to allow rotation thereof about a generally horizontal axis, and the source part being connected to the chassis part via a rotateable connection allowing the source part to rotate relative to the chassis part around a transverse axis, being aligned transverse to and intersecting with the horizontal axis; the source part comprising a source of therapeutic radiation directed towards the intersection of the transverse axis and the horizontal axis; the chassis part and the source part together defining an annular ring that encircles the horizontal axis.

In this way, the invention permits a radiotherapy apparatus to provide the full usual range of treatments, but also to adapt itself to adopt the geometry of WO2005/041774A1 when required, for example to treat difficult locations in the head and neck.

The source part will ideally also include a collimation apparatus for the therapeutic radiation, to ensure that the beam is appropriately shaped as required for the particular prescription being delivered.

The chassis part can comprise a source of diagnostic radiation and a detector for the imaging radiation, to allow the patient to be monitored prior to, during, and/or after treatment. The source of diagnostic radiation preferably emits a beam in a direction transverse to the direction of the therapeutic radiation so as to prevent scattering from the structure of the therapeutic source. To this end, the diagnostic beam can be emitted along the transverse axis. The detector can be moveable between a first position lying within the diagnostic beam and a second position that lies within the therapeutic beam in at least one relative position of the chassis part and source part; this permits the same detector to be used for either beam.

The source part can preferably rotate relative to the chassis part by way of at least one articulation between the two parts, ideally two. The diagnostic source is preferably located within the chassis part at a location closer to the horizontal axis than the at least one articulation. This allows the diagnostic beam to be aligned with the transverse axis without interfering with or scattering from the articulation. Where there are two articulations, these are ideally disposed around the annular ring on diametrically opposite sides of the horizontal axis, ensuring the correct geometry for the device. The chassis part ideally extends at least 180 degrees around the horizontal axis, and is capable of free rotation around the fixed support, i.e. rotation by more than 360°.

BRIEF DESCRIPTION OF THE DRAWINGS

An embodiment of the present invention will now be described by way of example, with reference to the accompanying figures in which;

FIG. 1 shows a part-sectional view along the horizontal axis of a radiotherapy apparatus according to the present invention; and FIG. 2 shows a vertical section through the radiotherapy apparatus of FIG. 1.

DETAILED DESCRIPTION OF THE EMBODIMENTS

Referring to FIGS. 1 and 2, a radiotherapy apparatus 10 is supported on a fixed stand 12 which is anchored to a floor or similar surface. The stand 12 has a circular aperture 14, around which a gantry 16 is mounted on suitable bearings to allow it to rotate freely around the aperture 14 around an axis of rotation 18 that is horizontal and centred within the aperture 14. An electrically-driven motor (not shown) is provided within the stand 12 to cause rotation of the gantry 16 when required.

The gantry 16 is annular or donut-shaped, with a central through-hole 20 which is aligned with the aperture 14 so as to create a space into which a patient 22 can be placed, supported by a patient table 24. The patient table 24 is of conventional construction and is capable of positional adjustment in all six degrees of freedom, i.e. three translational directions including extension into and through the through-hole 22 and three rotational directions. Thus, a patient can be positioned as desired relative to the apparatus 10, limited only by the need not to cause an impact between the patient table 24 or the patient 22, and the apparatus 10.

The gantry 16 is formed in two parts. A first part 26 is fixed in position (apart from its rotation) and is supported on the stand 12 by the bearings. It provides a chassis extending around the through-hole 20, on which is mounted the second part 28 which (as will be described below) carries the therapeutic radiation source. The two parts are mounted together via a rotateable connection 30a, 30b in the form of articulated joints one on either side of the annulus. These allow mutual rotation of the two parts around an axis 32 that is transverse to—in this case at 90° to—and intersects with the rotation axis 18 of the gantry. As the gantry rotates around the axis 18, it will of course carry the transverse axis 32 with it, and thus the absolute orientation of the axis 32 is not fixed. However, it will be apparent that its transverse and intersecting nature relative to the rotation axis 18 will be maintained throughout such rotation.

The second part 28 (or "source part") carries within it a linear accelerator 34 which is able to produce a relativistic beam of electrons 36, which is directed onto an x-ray target 38 in order to produce a therapeutic x-ray beam 40, in line with generally known principles. A multi-leaf collimator ("MLC") 42 is provided in order to shape the cross-sectional profile of the beam as required for a specific treatment, again in line with generally known principles. An example of a multi-leaf collimator is shown in EP-A-314,214, to which the reader is referred for a fuller understanding and which is hereby incorporated by reference.

The therapeutic x-ray beam 40 is directed from the target 38 through the MLC and directly towards the point of intersection of the rotation axis 18 and the transverse axis 32. Thus, as the gantry 16 rotates around the rotation axis 18, the beam 40 will be directed towards that point of intersection (the "isocentre") from all directions. The range of such directions created by a single rotation of the gantry 16 will sweep out a cone with its tip at the isocentre and with an internal angle defined by the approach angle of the beam itself defined by the relative rotational position of the chassis part 26 and the source part 28. By relative rotation of the chassis part 26 and the source part 28, a range of cone angles can be chosen, allowing the radiation delivery to be tailored to the anatomical structure of the patient 22 around the tumour to keep sensitive structures out of the beam.

In the relative orientation shown in FIG. 1 and in solid lines in FIG. 2, the beam 40 is directed towards the isocentre in a vertical plane (i.e. a cone with an internal angle of) 180°. It is thus perpendicular to both the rotation axis 18 and the transverse axis 32. In this state, the apparatus 10 shares the geometry of a conventional gantry-arm radiotherapy apparatus such as is shown in U.S. Pat. No. 6,888,919. By rotating the source part 28 relative to the chassis part 26 towards the position shown in dotted lines in FIG. 2, the approach angle of the beam 40 at the isocentre is moved so as to be acute relative to the rotation axis 18, and non-coplanar treatments can be carried out in (for example) to the head and neck region of the patient 22.

A diagnostic x-ray tube 44 and an imaging panel 46 are housed within the chassis part 26 of the gantry 16 in order to allow scanning of the patient 22 before, during and/or after treatment. The x-ray tube 44 is located on the transverse axis 32, inboard of the articulated joint 30a and directed so as to emit a beam 48 of kV radiation towards the central through-hole 20, centred on the transverse axis 32. It therefore creates a projected image of the volume around the isocentre; the imaging panel 46 is likewise located on the transverse axis 32, just inboard of the opposite articulated joint 30b in order to capture that image. As the image is taken along the same transverse axis 32 around which the source part 28 is articulated, it will capture an image of the treatment isocentre regardless of the angle at which the source part 28 is placed.

The imaging panel 46 is mounted on a guide 50 on which it is moveable along an arc such that it can be located in a range of positions, extending from that described above, just inboard of the articulated joint 30b and on the transverse axis 32, to a position 46' (shown in dotted lines) directly in the therapeutic beam 40 (when the source part 28 is also aligned accordingly). This allows it to be used as either an MV Imager or a kV imager. The arc of the guide 50 extends beyond 90° to enable imaging of a greater than nominal area in either of the positions.

The necessary shielding material associated with the imager can be incorporated into the gantry structure, and this may further facilitate the use of one common imager (where the imager is the same but the shielding material is different for kV and MV).

In this way, the full usual range of planar treatments can be provided, but when necessary the apparatus can adjust the angle between the chassis part 26 and the source part 28 to adopt a non-coplanar geometry. Despite this, the isocentre remains stationary, allowing treatments at various angles to be combined without having to reposition the patient and without losing the ability to image the patient.

It will of course be understood that many variations may be made to the above-described embodiment without departing from the scope of the present invention.

The invention claimed is:

1. A radiotherapy apparatus, comprising:
   a fixed support; and
   a gantry having an opening configured to receive a patient, the gantry comprising:
   a chassis part rotateably attached to the fixed support such that the chassis part is configured to rotate about a first rotation axis, the chassis part having an inner surface defining, at least in part, the opening of the gantry, and a source part mounted upon the chassis part, the source part being connected to the chassis part via at least one rotateable connection such that the source part is configured to rotate relative to the chassis part around a second rotation axis that is transverse to and intersects with the first rotation horizontal axis, wherein the source part comprises a source of therapeutic radiation configured to be directed towards the intersection of the first rotation axis and the second rotation axis, and wherein the chassis part and the source part define an annular ring that encircles the first rotation axis.

2. The radiotherapy apparatus of claim 1, wherein the source part includes a collimation apparatus for the therapeutic radiation.

3. The radiotherapy apparatus of claim 1, wherein the chassis part comprises:

a source of diagnostic radiation; and
a detector for the diagnostic radiation.

4. The radiotherapy apparatus of claim 3, wherein the source of diagnostic radiation is configured to emit a diagnostic radiation beam in a direction transverse to the direction of a therapeutic radiation beam emitted by the source of therapeutic radiation.

5. The radiotherapy apparatus of claim 4, wherein the source of diagnostic radiation is configured to emit the diagnostic radiation beam along the second rotation axis.

6. The radiotherapy apparatus of claim 4, wherein the detector is moveable between:

a first position lying within the diagnostic radiation beam emitted by the source of diagnostic radiation, and
a second position that lies within the therapeutic radiation beam in at least one relative position of the chassis part and source part.

7. The radiotherapy apparatus of claim 3, wherein the source part is configured to rotate relative to the chassis part by way of at least one articulation between the source part and the chassis part.

8. The radiotherapy apparatus of claim 7, wherein the source of diagnostic radiation is located within the chassis part at a location closer to the first rotation axis than the at least one articulation between the source part and the chassis part.

9. The radiotherapy apparatus of claim 1, wherein the source part and the chassis part are joined by a pair of articulations.

10. The radiotherapy apparatus of claim 9, wherein the two articulations are disposed around the annular ring on diametrically opposite sides of the first rotation axis.

11. The radiotherapy apparatus of claim 1, wherein the chassis part extends at least 180 degrees around the opening.

12. The radiotherapy apparatus of claim 1, wherein the chassis part is configured to rotate around the fixed support by more than 360 degrees.

13. The radiotherapy apparatus of claim 1, wherein the source part defines an incomplete ring which extends from one rotateable connection with the chassis part to a second rotateable connection with the chassis part.

14. The radiotherapy apparatus of claim 9, wherein the source part defines an incomplete ring which extends from the first articulation of the pair of articulations to the second articulation of the pair of articulations.

15. The radiotherapy apparatus of claim 1, wherein the first rotation axis extends between first and second ends of the opening of the gantry.

16. The radiotherapy apparatus of claim 1, wherein the source part is mounted upon an outer surface of the chassis part.

17. The radiotherapy apparatus of claim 16, wherein the source part and the chassis part are joined by a pair of articulated joints connecting an inner surface of the source part to the outer surface of the chassis part.

* * * * *

UNITED STATES PATENT AND TRADEMARK OFFICE
CERTIFICATE OF CORRECTION

PATENT NO. : 10,653,895 B2
APPLICATION NO. : 15/550007
DATED : May 19, 2020
INVENTOR(S) : Bergfjord Page 1 of 1

It is certified that error appears in the above-identified patent and that said Letters Patent is hereby corrected as shown below:

In the Claims

Claim 1, Column 5, Line 7, "intersects with the first rotation horizontal axis," should read --intersects with the first rotation axis,--.

Signed and Sealed this
First Day of September, 2020

Andrei Iancu
*Director of the United States Patent and Trademark Office*